(12) United States Patent
Michelson (10) Patent No.: US 6,749,636 B2
(45) Date of Patent: Jun. 15, 2004

(54) CONTOURED SPINAL FUSION IMPLANTS MADE OF BONE OR A BONE COMPOSITE MATERIAL

(76) Inventor: Gary K. Michelson, 438 Sherman Canal, Venice, CA (US) 90291

(*) Notice: Subject to any disclaimer, the term of this patent is extended or adjusted under 35 U.S.C. 154(b) by 18 days.

(21) Appl. No.: 10/112,746

(22) Filed: Apr. 2, 2002

(65) Prior Publication Data

US 2003/0120344 A1 Jun. 26, 2003

Related U.S. Application Data (60) Provisional application No. 60/281,187, filed on Apr. 3, 2001, and provisional application No. 60/281,112, filed on Apr. 2, 2001.

(51) Int. Cl.⁷ .................................................. A61F 2/44
(52) U.S. Cl. ..................................... 623/17.16; 606/61
(58) Field of Search .......................... 623/17.11, 17.16; 606/61, 73

(56) References Cited

U.S. PATENT DOCUMENTS

| | | | |
|---|---|---|---|
| 2,677,369 A | 5/1954 | Knowles |
| 3,848,601 A | 11/1974 | Ma et al. |
| 3,867,728 A | 2/1975 | Stubstad et al. |
| 3,875,595 A | 4/1975 | Froning |
| 3,905,047 A | 9/1975 | Long |
| D245,259 S | 8/1977 | Shen |
| 4,070,514 A | 1/1978 | Eatherly et al. |
| 4,309,777 A | 1/1982 | Patil |
| 4,349,921 A | 9/1982 | Kuntz |
| 4,501,269 A | 2/1985 | Bagby |
| RE31,865 E | 4/1985 | Roux |
| 4,599,086 A | 7/1986 | Doty |
| 4,636,217 A | 1/1987 | Ogilvie et al. |
| 4,714,469 A | 12/1987 | Kenna |
| 4,743,256 A | 5/1988 | Brantigan |
| 4,759,766 A | 7/1988 | Buettner-Janz et al. |
| 4,759,769 A | 7/1988 | Hedman et al. |
| 4,820,305 A | 4/1989 | Harms et al. |
| 4,834,757 A | 5/1989 | Brantigan |
| 4,863,477 A | 9/1989 | Monson |
| 4,877,020 A | 10/1989 | Vich |
| 4,878,915 A | 11/1989 | Brantigan |
| 4,904,261 A | 2/1990 | Dove et al. |
| 4,911,718 A | 3/1990 | Lee et al. |
| 4,936,848 A | 6/1990 | Bagby |
| 4,955,908 A | 9/1990 | Frey et al. |
| 5,015,247 A | 5/1991 | Michelson |
| 5,015,255 A | 5/1991 | Kuslich |
| 5,047,055 A | 9/1991 | Bao et al. |
| 5,059,193 A | 10/1991 | Kuslich |
| 5,062,845 A | 11/1991 | Kuslich et al. |
| 5,071,437 A | 12/1991 | Steffee |
| 5,122,130 A | 6/1992 | Keller |
| 5,123,926 A | 6/1992 | Pisharodi |
| 5,192,327 A | 3/1993 | Brantigan |

(List continued on next page.)

FOREIGN PATENT DOCUMENTS

| | | |
|---|---|---|
| EP | 0077159 | 4/1983 |
| EP | 0179695 | 4/1986 |
| EP | 0307241 | 3/1989 |

(List continued on next page.)

OTHER PUBLICATIONS

Crock, H.V.; Practice of Spinal Surgery; Springer–Verlag/Wien, New York (1983).

(List continued on next page.)

*Primary Examiner*—David J. Isabella
*Assistant Examiner*—Thomas J Sweet
(74) *Attorney, Agent, or Firm*—Martin & Ferraro, LLP (57) ABSTRACT

An interbody spinal implant made of cortical bone or a bone composite adapted for placement across an intervertebral space formed across the height of a disc space between two adjacent vertebral bodies. The implant has a leading end that includes at least a portion of an arc of a circle from side to side, and sides that are at least in part straight or a trailing end having a radius of curvature of another circle from side to side.

136 Claims, 7 Drawing Sheets

U.S. PATENT DOCUMENTS

| | | | |
|---|---|---|---|
| 5,246,458 A | 9/1993 | Graham | |
| 5,258,031 A | 11/1993 | Salib et al. | |
| 5,306,308 A | 4/1994 | Gross et al. | |
| 5,306,309 A | 4/1994 | Wagner et al. | |
| 5,370,697 A | 12/1994 | Baumgartner | |
| 5,397,364 A | 3/1995 | Kozak et al. | |
| 5,425,772 A | 6/1995 | Brantigan | |
| 5,443,514 A | 8/1995 | Steffee | |
| 5,458,638 A | 10/1995 | Kuslich et al. | |
| 5,507,813 A | 4/1996 | Dowd et al. | |
| 5,571,109 A | 11/1996 | Bertagnoli | |
| D377,527 S | 1/1997 | Michelson | |
| 5,609,635 A * | 3/1997 | Michelson | 623/17.16 |
| 5,669,909 A | 9/1997 | Zdeblick et al. | |
| 5,683,463 A | 11/1997 | Godefroy et al. | |
| 5,702,449 A | 12/1997 | McKay | |
| 5,766,252 A | 6/1998 | Henry et al. | |
| 5,776,199 A * | 7/1998 | Michelson | 623/17.16 |
| 5,782,919 A | 7/1998 | Zdeblick et al. | |
| D397,439 S | 8/1998 | Koros et al. | |
| 5,800,547 A | 9/1998 | Schafer et al. | |
| 5,814,084 A | 9/1998 | Grivas et al. | |
| 5,846,484 A * | 12/1998 | Scarborough et al. | 422/28 |
| 5,861,041 A | 1/1999 | Tienboon | |
| 5,865,845 A | 2/1999 | Thalgott | |
| 5,888,222 A | 3/1999 | Coates et al. | |
| 5,899,939 A | 5/1999 | Boyce et al. | |
| 5,972,368 A | 10/1999 | McKay | |
| 5,989,289 A | 11/1999 | Coates et al. | |
| 6,033,438 A | 3/2000 | Bianchi et al. | |
| 6,037,519 A | 3/2000 | McKay | |
| 6,039,762 A | 3/2000 | McKay | |
| D425,989 S | 5/2000 | Michelson | |
| 6,083,228 A | 7/2000 | Michelson | |
| 6,113,638 A | 9/2000 | Williams et al. | 623/17.11 |
| 6,136,031 A | 10/2000 | Middleton | 623/17.11 |
| 6,143,032 A | 11/2000 | Schafer et al. | |
| 6,174,311 B1 | 1/2001 | Branch et al. | |
| 6,179,875 B1 | 1/2001 | Von Strempel | |
| 6,200,347 B1 | 3/2001 | Anderson et al. | |
| 6,206,923 B1 | 3/2001 | Boyd et al. | |
| 6,224,607 B1 | 5/2001 | Michelson | |
| 6,231,610 B1 | 5/2001 | Geisler | |
| 6,241,770 B1 | 6/2001 | Michelson | |
| 6,241,771 B1 | 6/2001 | Gresser et al. | |
| 6,245,108 B1 | 6/2001 | Biscup | |
| 6,258,125 B1 | 7/2001 | Paul et al. | |
| 6,261,586 B1 | 7/2001 | McKay | |
| 6,277,149 B1 | 8/2001 | Boyle et al. | |
| 6,294,041 B1 | 9/2001 | Boyce et al. | |
| 6,294,187 B1 | 9/2001 | Boyce et al. | |
| 6,342,074 B1 | 1/2002 | Simpson | 623/17.11 |
| 6,348,071 B1 | 2/2002 | Steffee et al. | 623/17.15 |
| 6,350,283 B1 | 2/2002 | Michelson | |
| 6,371,988 B1 | 4/2002 | Pafford et al. | 623/17.11 |
| 6,383,221 B1 | 5/2002 | Scarborough et al. | |
| 6,395,031 B1 | 5/2002 | Foley et al. | |
| 6,402,785 B1 | 6/2002 | Zdeblick et al. | |
| 6,423,095 B1 * | 7/2002 | Van Hoeck et al. | 623/17.16 |
| 6,468,311 B2 | 10/2002 | Boyd et al. | 623/17.16 |
| 6,471,724 B2 * | 10/2002 | Zdeblick et al. | 623/17.16 |
| 6,511,509 B1 | 1/2003 | Ford et al. | |
| 6,562,072 B1 | 5/2003 | Fuss et al. | |
| 2001/0018614 A1 | 8/2001 | Bianchi | |
| 2001/0031254 A1 | 10/2001 | Bianchi et al. | |
| 2002/0035401 A1 | 3/2002 | Boyce et al. | |
| 2002/0099444 A1 | 7/2002 | Boyd et al. | |
| 2002/0107571 A1 | 8/2002 | Foley | |

FOREIGN PATENT DOCUMENTS

| | | |
|---|---|---|
| EP | 0577179 | 1/1994 |
| EP | 0599419 | 6/1994 |
| EP | 0627204 | 12/1994 |
| EP | 0637440 | 11/1997 |
| ES | 283078 | 5/1985 |
| FR | 2703580 | 10/1994 |
| JP | 57/029348 | 9/1982 |
| JP | 62/155846 | 7/1987 |
| WO | WO 93/01771 | 2/1993 |
| WO | WO 95/08306 | 3/1995 |
| WO | WO 95/08964 | 4/1995 |
| WO | WO 96/22747 | 8/1996 |
| WO | WO 99/63891 | 12/1999 |
| WO | WO 00/74608 | 12/2000 |
| WO | WO 01/28465 | 4/2001 |
| WO | WO 01/68005 | 4/2001 |
| WO | WO 01/62191 | 8/2001 |
| WO | WO 01/68004 | 9/2001 |
| WO | 01/80785 * | 11/2001 |

OTHER PUBLICATIONS

DeBowes, R.M. et al.; Study of Bovine . . . Steel Baskets; Transactions of the 29$^{th}$ Annual Meeting; Orthopaedic Research Society, vol. 8, p. 407, Mar. 8–10 (1983).

Otero–Vich, Jose M.; Anterior Cervical Interbody Fusion with Threaded Cylindrical Bone; J. Neurosurg 63:750–753 (Nov. 1985).

Itoman, M., et al.; Banked Bone grafting for Bone Defect Repair–Clinical Evaluation of Bone Union and Graft Incorporation; J. Jpn. Orthop. Assoc. 62:461–469 (1988).

Schmitz et al.; Performance of Alloplastic Materials and Design of an Artificial Disc; the Artificial Disc. Brock, Mayer, Weigel; pp. 23–34 (1991).

Laparoscopic Bone Dowel Surgical Technique; Brochure of Sofamor Danek (1995).

Brochure of University of Florida Tissue Bank; MD–I and MD–II Custom Machine Cortical Dowels; (*Circa* 1996).

Brochure of University of Florida Tissue Bank; MD–III Threaded Cortical Dowel; (*Circa* 1996).

Zindrick, et al.; Lumbar Spine Fusion: Different Types and Indications; The Lumbar Spine, vol. 1, Second Edition, pp. 588–593 (1996).

Ray, C.D.; Spinal Interbody Fusions: A Review, Featuring New Generation Techniques; Neurosurgery Quarterly, 7(2):135–156 (1997).

RTI Precision Machined Allograft: The Surgeon's Choice, Brochure by Regeneration Technologies, Inc. (2000).

A picture of a Medtronic, Sofamor Danek Display; titled "Evolving With Your Needs" (Apr. 2000).

What's New at . . . Spine–Tech: Allograft and Thoracolumbar, Brochure Spine–Tech (*Circa* 2001).

Puros ALIF Bone Graft, Brochure by Sulzer Spine–Tech (2001).

New IBS Allograft, The C–TLIF Approach, Brochure of OrthoDevelopment (2002).

Introducing graftech Allografts, Webpage by Osteotech (*Circa* Jan. 2002).

RTI Tissue Services, Spinal Allograft, Webpage of Regeneration Technologies, Inc. (2002).

Muschler, et al.; The Biology of Spinal Fusion; Spinal Fusion Science and Technique, Cotler and Cotler, pp. 9–13 (Undated).

* cited by examiner

FIG. 14

CONTOURED SPINAL FUSION IMPLANTS MADE OF BONE OR A BONE COMPOSITE MATERIAL

RELATED APPLICATIONS

This application claims priority to provisional application No. 60/281,187, filed Apr. 3, 2001, and provisional application No. 60/281,112, filed Apr. 2, 2001, both of which are incorporated by reference herein.

FIELD OF THE INVENTION

The present invention relates generally to interbody spinal implants preferably adapted for placement into an implantation space created across the height of a disc space between two adjacent vertebral bodies for the purpose of correcting spinal disease at that interspace. The spinal implants are made of an implant material that is bone or a bone composite. The implants are adapted such that fusion occurs at least in part through the implants.

DESCRIPTION OF THE RELATED ART

The diaphysis is the shaft of a major long bone between the epiphyses, the ends of the bone forming the joints. Human cadaveric diaphyseal bone is used to form implants made of bone utilized in interbody spinal fusion surgery.

A diaphyseal ring is formed by making two spaced apart cuts approximately perpendicular to the long axis of the diaphyseal portion of a major long bone with the medullary canal forming an opening through the ring. Such rings are generally harvested from femurs for use in the lumbar spine. Other bones from the arm or leg or other part of the human skeleton may be useful in various regions of the spine.

The cuts are generally spaced apart so as to form a ring of bone having a height corresponding to the restored disc space or slightly greater. Diaphyseal ring bone grafts are placed into the spine within and across the height of the space previously occupied by a spinal disc between adjacent vertebral bodies to achieve interbody fusion of those vertebral bodies through the disc space. The diaphyseal ring bone graft is incorporated into the bony fusion over time.

Interbody spinal fusion with diaphyseal bone rings, however, has had limited success in the past. While all the causes for failure may not yet be appreciated, it is nevertheless believed that a failure to gain congruity at the interfaces of the bone ring implant to the adjacent vertebral bodies, and a failure to achieve stability of the bone ring implant, may be two of the more significant factors subject to the surgeon's control contributing to such failures.

At the time of surgery, where fusion is intended to occur between adjacent vertebral bodies of a patient's spine, the surgeon typically prepares an opening at the site of the intended fusion by removing some or all of the disc material that exists between the adjacent vertebral bodies to be fused. Because the outermost layers of bone of the vertebral end plate are relatively inert to new bone growth, the surgeon must work on the end plate to remove at least the outermost cell layers of bone to gain access to the blood-rich, vascular bone tissue within the vertebral body. In this manner, the vertebrae are prepared in a way that encourages new bone to grow into or through an implant that is placed between the vertebral bodies.

Present methods of forming this space between adjacent vertebral bodies generally include the use of one or more of the following: hand held biting and grasping instruments known as rongeurs; drills and drill guides; rotating burrs driven by a motor; osteotomes and chisels, and a double wheel cutter or vertebral interspace preparation device. In particular, the double wheel cutter or vertebral interspace preparation device, as disclosed by Michelson in WO 99/63891, incorporated herein by reference, is adapted for linear insertion, i.e., insertion along a single axis, and without the need to substantially move the device from side to side within the disc space along a second axis. In such a preferred embodiment, the device has at its working end an abrading element having a width generally corresponding to the width of the implant to be implanted.

There is a desire to improve congruity at the interfaces of the implant to the adjacent vertebral bodies, and to achieve stability of the implant. Therefore it is advantageous for the contour of the implants to closely match the implantation space formed between and at least in part into the adjacent vertebral bodies to allow a more uniform load transfer across the implant between the vertebral bodies.

Interbody spinal implants that are entirely or almost entirely made of cortical bone or a bone composite material offer the advantages of that material including an appropriate modulus of elasticity and strength for the prescribed use, the capacity to be bioactive, including being osteoconductive, osteoinductive, osteogenic, and to more generally provide a good substrate for the formation of new bone as fusion occurs. Further, by being bioabsorable the bone material is replaced by the patient's own bone over time, thereby preventing stress shielding and leading to the eventual elimination of any foreign body from the implantation site.

As it is desirable to take advantage of all these benefits, there exists a need for an improved interbody spinal fusion implant made of bone or a bone composite material having a configuration that provides for an improved congruity of the implant to the vertebral bodies and improved implant stability.

SUMMARY OF THE INVENTION

In accordance with the purposes of the present invention, as embodied and broadly described herein, an interbody spinal fusion implant made of cortical bone is provided for insertion at least in part into an implantation space formed across the height of a disc space between adjacent vertebral bodies of a human spine. The implant includes a leading end for insertion first into the disc space and a trailing end opposite the leading end. The implant has a length from the leading end to the trailing end. The leading end is configured in the shape of half a circle from side to side. The implant also includes opposed upper and lower portions between the leading and trailing ends that are adapted to be placed within the disc space to contact and support the adjacent vertebral bodies. The upper and lower portions are non-arcuate along at least a portion of the length of the implant. The implant also includes opposite sides between the upper portion and lower portion, and between the leading and trailing ends. At least one of the opposite sides is at least in part straight along at least a portion of the length of the implant.

In accordance with the purposes of the present invention, as embodied and broadly described herein, an interbody spinal fusion implant made of cortical bone is provided for insertion at least in part into an implantation space formed across the height of a disc space between adjacent vertebral bodies of a human spine. The implant includes a leading end for insertion first into the disc space and a trailing end opposite the leading end. The implant has a length from the leading end to the trailing end. The leading end is configured from side to side in the shape of approximately one half of a first circle. The trailing end has a radius of curvature of a second circle from side to side. The second circle has a radius greater than the radius of the first circle. The implant also includes opposed upper and lower portions between the leading and trailing ends that are adapted to be placed within the disc space to contact and support the adjacent vertebral bodies. The implant has a maximum width that is greater than one-half of the width of the adjacent vertebral bodies into which the implant is adapted to be inserted.

The implants of the present invention are preferably manufactured from a bone ring obtained from a major long bone of a human having a medullary canal. The implant includes at least a portion of the medullary canal passing through the upper and lower portions to form a passage adapted to hold bone growth promoting material for permitting for the growth of bone from vertebral body to vertebral body through the passage. In another preferred embodiment, the implants of the present invention are manufactured from a bone composite material.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

DETAILED DESCRIPTION OF THE INVENTION

The following description is intended to be representative only and not limiting and many variations can be anticipated according to these teachings, which are included within the scope of this inventive teaching. Reference will now be made in detail to the preferred embodiments of this invention, examples of which are illustrated in the accompanying drawings. Wherever possible, the same reference numbers will be used throughout the drawings to refer to the same or like parts.

Figure 1:
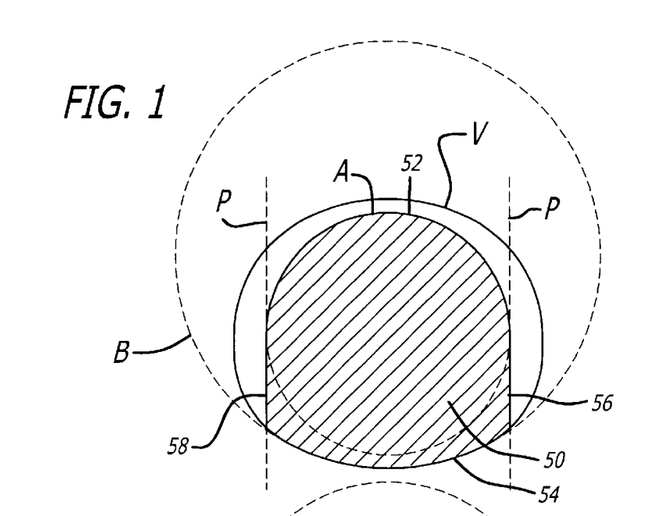
FIG. 1 is a top plan view of a vertebral body in the lumbar spine with an implantation space formed to receive a spinal implant having a radius of curvature at the leading end that is less than the radius of curvature of the trailing end of the anterior aspect of the vertebral body between the sides of the implantation space.
Figures 2, 5:
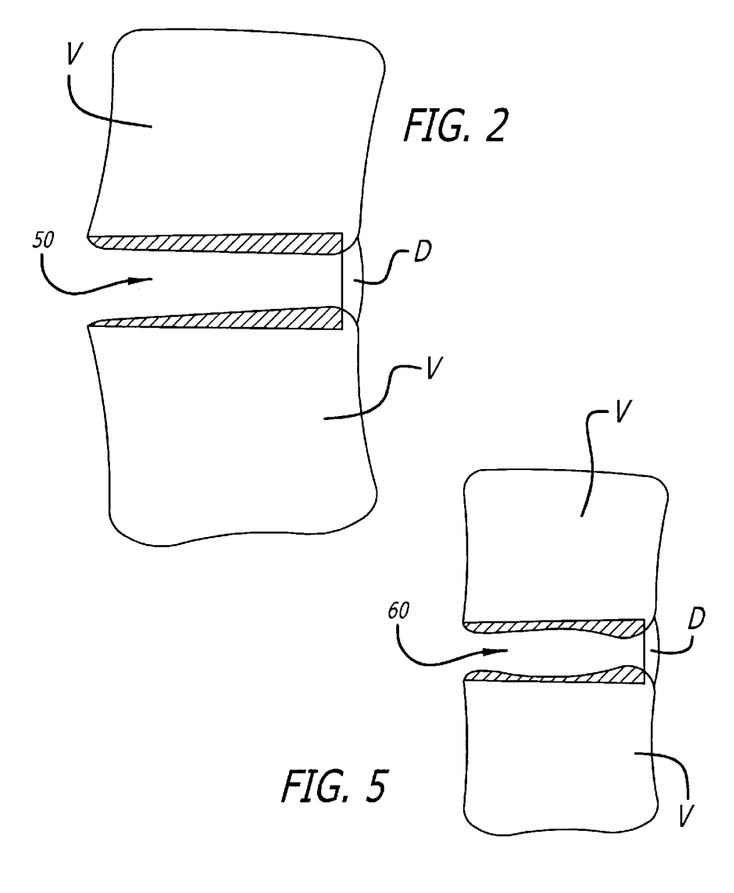
FIG. 2 is a side elevation view of two adjacent vertebral bodies in the lumbar spine with the implantation space of FIG. 1 formed across the height of the spinal disc and into the adjacent vertebral bodies.
FIG. 5 is a side elevation view of two adjacent vertebral bodies in the cervical spine with the implantation space of FIG. 4 formed across the height of the spinal disc and into the adjacent vertebral bodies.
Figure 3:
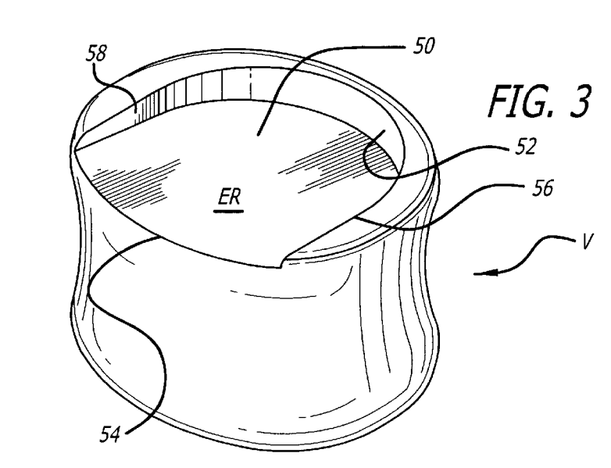
FIG. 3 is a side perspective view of the implantation space of FIG. 1.

FIGS. 1–3 show an implantation space 50 formed across the height of the space occupied by a spinal disc D and into vertebral bodies V in the lumbar spine. Implantation space 50 is preferably formed with the apparatus and method disclosed by Michelson in U.S. Pat. No. 6,083,228, and WO 99/63891, the disclosures of which are both incorporated herein by reference. The instruments and method are not the subject matter of this application. It is understood that the preparation of the implantation space shown therein are a preferred instrument and method of preparing the implantation spaces and that any method and instrumentation suitable for the purpose may be utilized to prepare the desired implantation space.

Implantation space 50 is preferably formed in the endplate region ER in the subchondral bone of the vertebral body V. Implantation space 50 preferably is formed to have a leading edge 52 with a shape from side to side of approximately one-half of a first circle A. The trailing portion 54 of implantation space 50 preferably includes at least a portion of the anterior aspect of the vertebral body having a radius of curvature of a second circle B from side to side. Preferably the radius of circle A is less than the radius of circle B. Implantation space 50 may further include side edges 56, 58. Side edges 56, 58 preferably include at least a straight portion, may be parallel to one another along lines P and form a curved transition with leading edge 52.

Figure 4:
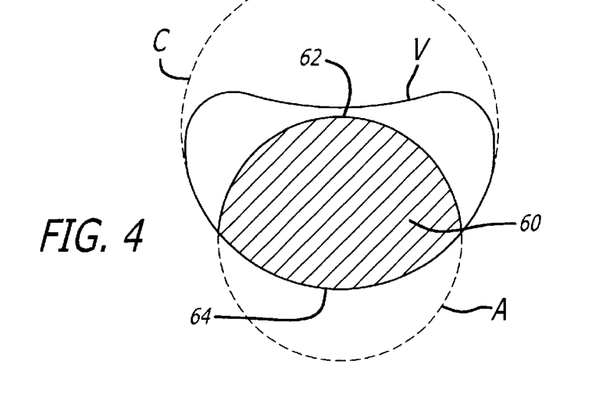
FIG. 4 is a top plan view of a vertebral body in the cervical spine with an implantation space formed to receive a spinal implant having a radius of curvature at the leading end that is less than the radius of curvature of the trailing end of the anterior aspect of the vertebral body.
Figure 6:
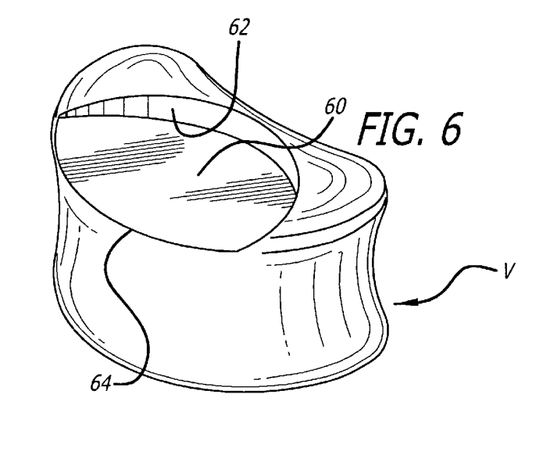
FIG. 6 is a side perspective view of the implantation space of FIG. 4.

FIGS. 4–6 show an implantation space 60 formed across the height of the space occupied by a spinal disc D and into vertebral bodies V in the cervical spine. Implantation space 60 preferably is formed to have a leading edge 62 with a shape from side to side of approximately one half of a first circle A. The trailing portion of implantation space 60 preferably includes at least a portion of the anterior aspect of the vertebral body having a radius of curvature of a second circle C from side to side. Preferably the radius of circle A is less than the radius of circle C. Implantation space 60, however, preferably does not have straight side edges like implantation space 50 because the anterior to posterior depth of cervical vertebral bodies is less than the anterior to posterior depth of lumbar vertebral bodies. Thus, the radius of circle C is smaller in the cervical spine than the radius of circle B in the lumbar spine.

FIGS. 7–12 show an implant 100 in accordance with a preferred embodiment of the present invention. Implant 100 has a leading end 102 for insertion first into the disc space between two adjacent vertebral bodies and a trailing end 104 opposite leading end 102, and opposite sides 110, 112 therebetween. Leading end 102 is preferably configured to match the contour of leading edge 52 of implantation space 50 and trailing end 104 is preferably configured to conform to the contour of the anterior aspect of the vertebral body at trailing portion 54 of implantation space 50. Sides 110, 112 are generally planar and preferably correspond to the configuration of side edges 56, 58 of implantation space 50.

Figures 7, 8:
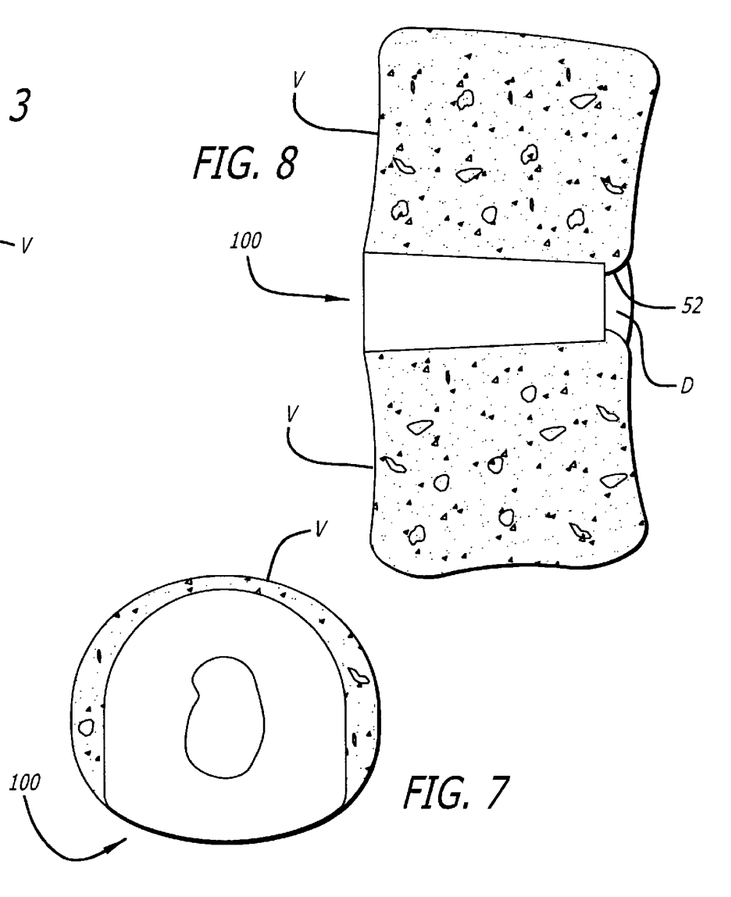
FIG. 7 is a top plan view of a vertebral body in the lumbar spine and a preferred embodiment of a bone implant in accordance with the present invention installed into the implantation space of FIG. 1.
FIG. 8 is a side elevation view of two adjacent vertebral bodies with the implant of FIG. 7 installed into the implantation space of FIG. 1 formed across the height of the spinal disc and into the adjacent vertebral bodies.
Figures 9, 10, 11, 12, 13:
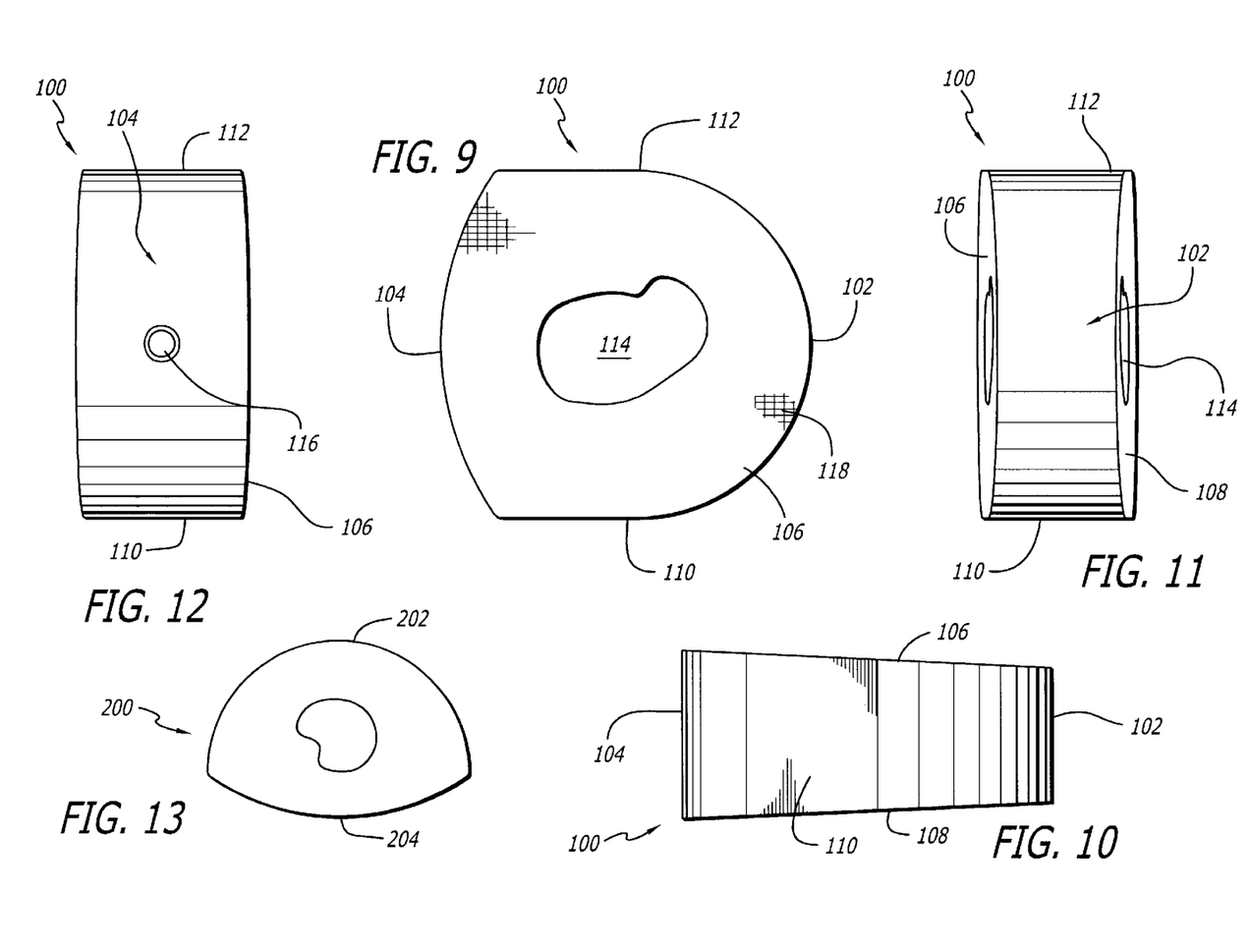
FIG. 9 is a top plan view of the implant of FIG. 7.
FIG. 10 is a side elevation view of the implant of FIG. 7.
FIG. 11 is a leading end view of the implant of FIG. 7.
FIG. 12 is a trailing end view of the implant of FIG. 7.
FIG. 13 is a top plan view of another preferred embodiment of a bone implant in accordance with the present invention for use in the implantation space of FIG. 4.

In a preferred embodiment of the present invention, leading end 102, trailing end 104, and opposite sides 110, 112 are machined to have various configurations. Leading end 102 is preferably machined to have a shape of approximately half a first circle from side to side. Where the implantation space is prepared into the vertebral bodies to have a lip or ridge that is at least in part curved, leading end 102 may be adapted to abut at least that portion of the implantation space.

One or both of sides 110, 112 may also be formed to be at least in part oriented generally parallel to the mid-longitudinal axis of implant 100 and/or to each other. Further, leading end 102 may be tapered to facilitate insertion of implant 100 between the two adjacent vertebral bodies.

Trailing end 104 preferably forms an arc of a second circle from side to side having a radius greater than the radius of the first circle associated with leading end 102. Preferably, at least a portion of trailing end 104 is adapted to conform to at least a portion of the peripheral contour of the anterior aspect of the vertebral bodies adjacent the disc space into which the implant is adapted to be inserted, though the invention is not so limited.

FIG. 12 shows that implant 100 preferably has a driver opening 116 at trailing end 104 for cooperatively engaging an instrument for installing implant 100 into the implantation space. Driver opening 116 is preferably configured for threaded engagement with an insertion instrument.

FIGS. 8, 10, and 11 show at least a portion of upper and lower surfaces 106, 108 in an angular relationship to each other from trailing end 104 to leading end 102 for allowing for angulation of the adjacent vertebral bodies relative to each other. Preferably, upper and lower surfaces 106, 108 are non-arcuate in a direction along the mid-longitudinal axis of implant 100. Implant 100 preferably has a maximum height that is less than the maximum width of the implant.

As shown in FIG. 9, upper and lower surfaces 106, 108 preferably have a passage 114 passing therethrough between leading and trailing ends 102, 104, respectively, and opposite sides 110, 112. Passage 114 is preferably adapted to hold bone growth promoting material to permit for the growth of bone from vertebral body to vertebral body through passage 114. In addition to passage 114, upper and lower surfaces 106, 108 may include at least one opening in communication with one another to permit for the growth of bone from vertebral body to vertebral body through implant 100, though the invention is not so limited. Upper and lower surfaces 106, 108 may also be porous and may include a bone ingrowth surface.

As shown in FIG. 9, the implants described herein may include a bone-engaging surface 118 such as knurling for example. Bone engaging surface 118 is configured to engage the bone of the adjacent vertebral bodies to maintain implant 100 within the adjacent vertebral bodies after implantation. Other preferred embodiments of bone-engaging surfaces may include the surfaces of the implant being roughened, ratcheted, splined, or may include at least one protrusion to penetrably engage the bone of the vertebral bodies. By way of example only, the implants of the present invention may include the surface configuration taught by Michelson in U.S. patent application Ser. No. 09/457,228, entitled "Spinal Implant Surface Configuration," the disclosure of which is incorporated by reference herein.

Implant 100 is preferably, but need not be manufactured from a diaphyseal bone ring. The diaphyseal bone ring is preferably obtained from a major long bone of the human skeleton. The bone ring is formed by making two spaced apart cuts approximately perpendicular to the long axis of the diaphyseal portion of the major long bone with a portion of the medullary canal forming an opening through the ring. Such rings are generally harvested from femurs for use in the lumbar spine. Other bones from the arm or leg or other part of the human skeleton may be useful in various regions of the spine. The cuts may be made into the long bone generally perpendicular to or at other angles transverse to the long axis of the diaphyseal bone to form the bone ring having upper and lower surfaces. Making the cuts at an angle to each other creates a bone ring with upper and lower surfaces that are angled relative to each other. The angular relationship of the upper and lower surface of the bone ring, when subsequently formed into an implant and implanted into the spine, position the adjacent vertebral bodies in angular relationship to each other to restore the natural curvature of the spine, such as lordosis for example.

The bone may be machined to form an implant having a selected shape suitable for the intended purpose. Examples of tools which may be used to machine the implant include, but are not limited to, burrs, reamers, mills, saws, trephines, chisels, and the like. For example only, the leading end may be shaped to be approximately half a circle from side to side. The sides may be machined to be at least in part straight. The trailing end may be machined to any desired shape suitable for the intended purpose and may preferably be shaped to conform to the anatomical contour of the adjacent vertebral bodies between which the implant is adapted to be inserted. The medullary canal preferably forms a passage adapted to hold bone growth promoting materials and/or substances. Where it is appropriate, it may be desirable to preserve at least a portion of the natural curvature of the perimeter of the bone ring as part of the configuration of the implant shape.

Implant 100 preferably has a length greater than one-half the depth of the vertebral bodies adjacent the disc space into which the implant is adapted to be inserted as measured between the anterior and posterior aspects of the vertebral bodies. Implant 100 also preferably has a maximum width that is greater than one-half the width of the adjacent vertebral bodies into which the implant is adapted to be inserted.

For any of the embodiments of the implants of the present invention, instead of being machined from a single bone portion, the implant can be manufactured from a composite bone material which may include at least one of cortical bone fibers, bone filaments, bone particles, or bone dust, and a binding material which may or may not be bioactive and/or bioresorbable such as a plastic, ceramic, for example. By way of example only and not limitation, bioresorbable materials may include polygalactone. Once formed, the composite implant material may be machined or molded, into the desired shape.

FIG. 13 shows another preferred embodiment of the present invention for use in the cervical spine generally referred to by the numeral 200. Implant 200 is preferably configured to conform to the shape of implantation space 60 formed in the endplates of adjacent cervical vertebral bodies with instrumentation and methods similar to those used in association with the lumbar spine but modified for use in the cervical spine. Implant 200 may, for example, have a leading end 202 formed to have a shape of approximately one-half a first circle from side to side. Trailing end 204 preferably may be formed as an arc of a second circle from side to side that intersects the curvature of leading end 202 from side to side. The radius of the second circle associated with trailing end 204 is preferably greater that the radius of the first circle associated with leading end 202.

Figure 14:
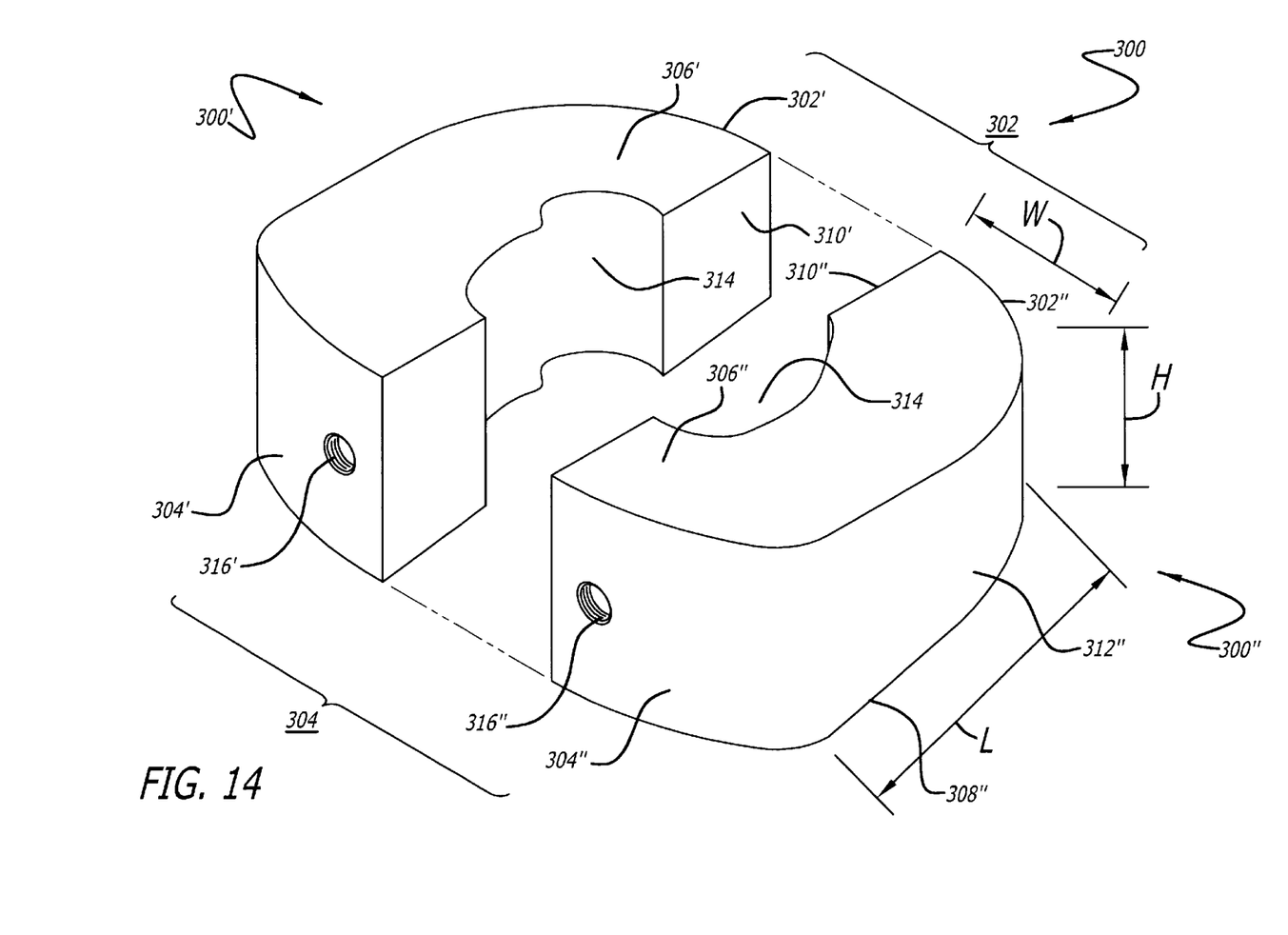
FIG. 14 is a rear perspective view of another preferred embodiment of a bone implant in accordance with another preferred embodiment of the present invention having two members that are preferably mirror images of one another.
Figures 15, 16, 17, 18, 19:
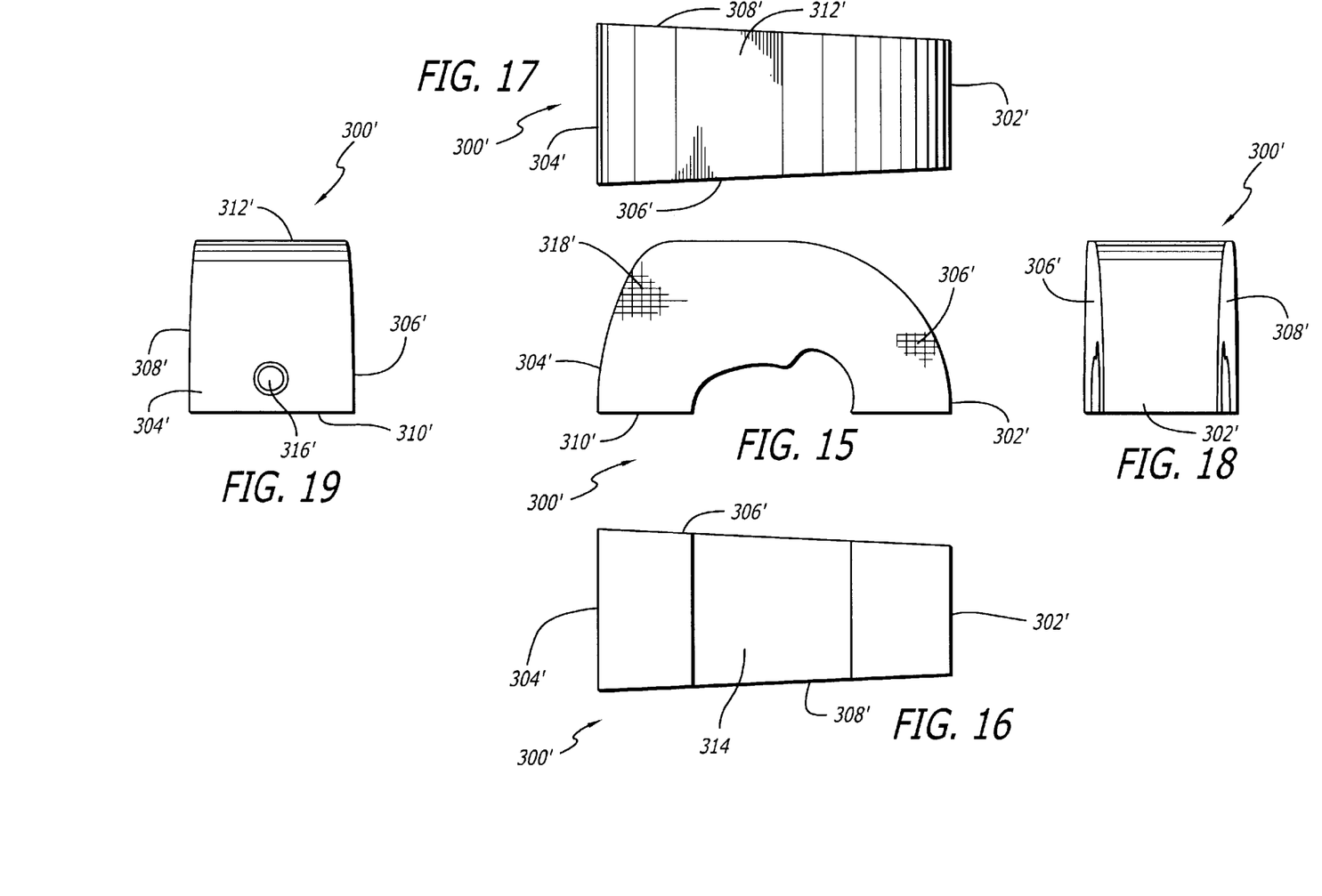
FIG. 15 is a top plan view of one of the members of the implant of FIG. 14.
FIG. 16 is an interior side elevation view of one of the members of the implant of FIG. 14.
FIG. 17 is an exterior side elevation view of one of the members of the implant of FIG. 14.
FIG. 18 is a leading end view of one of the members of the implant of FIG. 14.
FIG. 19 is a trailing end view of one of the members of the implant of FIG. 14.

FIGS. 14–19 show an implant 300 in accordance with another preferred embodiment of the present invention adapted for use from the anterior approach to the spine. FIG. 14 shows a rear perspective view of implant 300. Implant 300 includes at least two members 300', 300" that are adapted to be placed side by side with one another. Member 300' is preferably, but need not be a mirror image of member 300". The description of member 300' is equally applicable to member 300". Member 300' has a leading portion 302' for insertion first into the disc space between two adjacent vertebral bodies and a trailing portion 304' opposite leading portion 302'. Member 300' has a top 306', a bottom 308', an interior side 310', and an exterior facing side 312' opposite interior facing side 310'. As used herein, the phrase "interior side" describes the side of the member adapted to be orientated toward the interior side of another member when a pair of members are inserted side by side into the disc space. In a preferred embodiment, interior side 310' includes at least a portion of the medullary canal of the bone ring.

Leading portions 302', 302" of each member 300', 300", respectively, form leading end 302 of implant 300 when the members are placed side by side to one another. Leading end 302 of implant 300 is preferably configured in the shape of one-half a first circle from side to side. Trailing end 304, composed of trailing portions 304', 304" when members 300', 300" are placed side by side to one another, may, but need not be formed as an arc of a second circle side to side having a radius greater than a radius of the first circle associated with leading end 302 of implant 300.

Member 300' is placed side by side with member 300" so that the portion of the medullary canal of interior side 310' of each member are adjacent one another to form a passage 314 through implant 300. Preferably passage 314 is adapted to hold bone growth promoting material to permit for the growth of bone from vertebral body to vertebral body through passage 314. Member 300' preferably has a maximum width W that is less than approximately one-half the width of the adjacent vertebral bodies into which the member is adapted to be inserted. Also, the combined width of both members 300', 300" is preferably greater than one-half the width of the adjacent vertebral bodies into which the members are adapted to be inserted.

Members 300', 300" provide the added advantage in that each member can be inserted through a smaller space than a single larger implant, to achieve the same effect as the larger implant.

Figure 20:
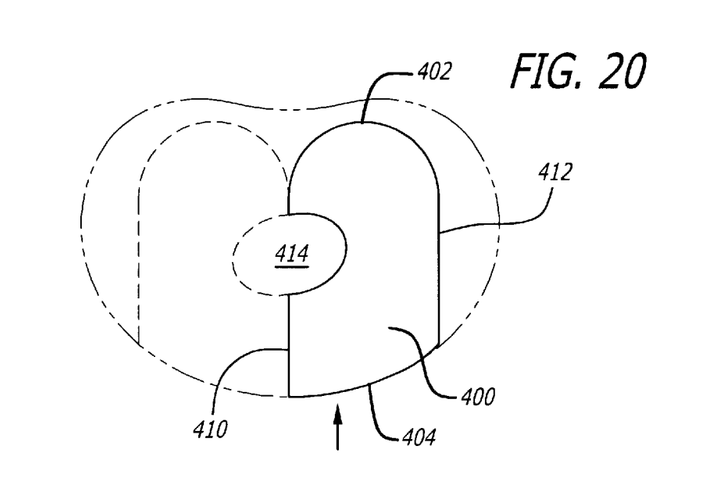
FIG. 20 is a top plan view of another preferred embodiment of a bone implant in accordance with the present invention and a second bone implant that is a mirror image thereof illustrated in dashed line, both implants being shown implanted from an anterior approach to the spine in a vertebral body illustrated in dashed line.

FIG. 20 shows an implant 400 in accordance with another preferred embodiment of the present invention adapted for use from an anterior approach to the spine. Implant 400 is similar to implant 100 and has a leading end 402 that is shaped as approximately one-half a first circle. Implant 400 is adapted to have a maximum width between sides 410, 412 that is less than one-half of the width of the adjacent vertebral bodies into which implant 400 is adapted to be inserted. Trailing end 404 forms an arc of a second circle having a radius that is substantially greater than the radius of the first circle associated with leading end 402.

Figure 21:
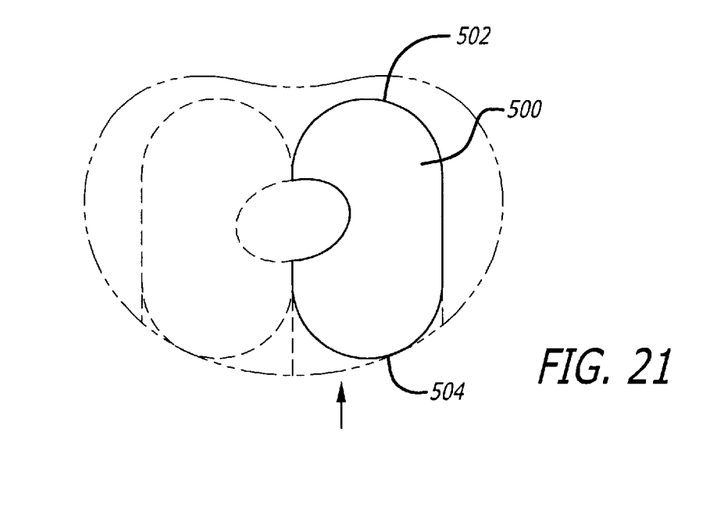
FIG. 21 is a top plan view of another preferred embodiment of a bone implant in accordance with the present invention and a second bone implant that is a mirror image thereof illustrated in dashed line, both implants being shown implanted from an anterior approach to the spine in a vertebral body illustrated in dashed line.

FIG. 21 shows an implant 500 in accordance with another preferred embodiment of the present invention adapted for use from an anterior approach to the spine. Implant 500 is similar to implant 400 except that both leading end 502 and trailing end 504 are preferably in the shape of a half circle side to side.

Figure 22:
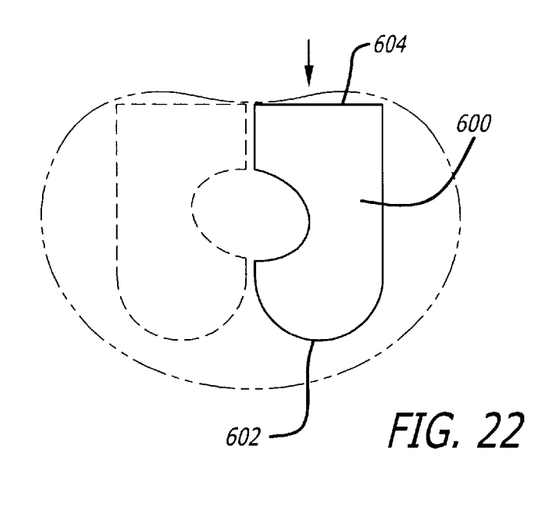
FIG. 22 is a top plan view of another preferred embodiment of a bone implant in accordance with the present invention and a second bone implant that is a mirror image thereof illustrated in dashed line, both implants being shown implanted from a posterior approach to the spine in a vertebral body illustrated in dashed line.

FIG. 22 shows an implant 600 in accordance with another preferred embodiment of the present invention adapted for use from a posterior approach to the spine. Implant 600 is similar to implant 400 except that trailing end 604 is preferably at least in part straight from side to side.

FIGS. 23–29 show an implant 700 in accordance with another embodiment of the present invention. Implant 700 is similar to implant 100 and has a leading end 702 in the shape of approximately one-half a first circle A and a trailing end 704 formed as an arc of a second circle C. Implant 700 preferably includes straight portions 711, 713 along at least a portion of sides 710, 712, respectively, that are preferably parallel to each other along lines P. Implant 700 also preferably includes a curved transition from each straight portion 711, 713 of sides 710, 712, respectively, to trailing end 704 to form rounded portions 715, 717, respectively.

Figures 23, 24, 25, 26, 27, 28, 29:
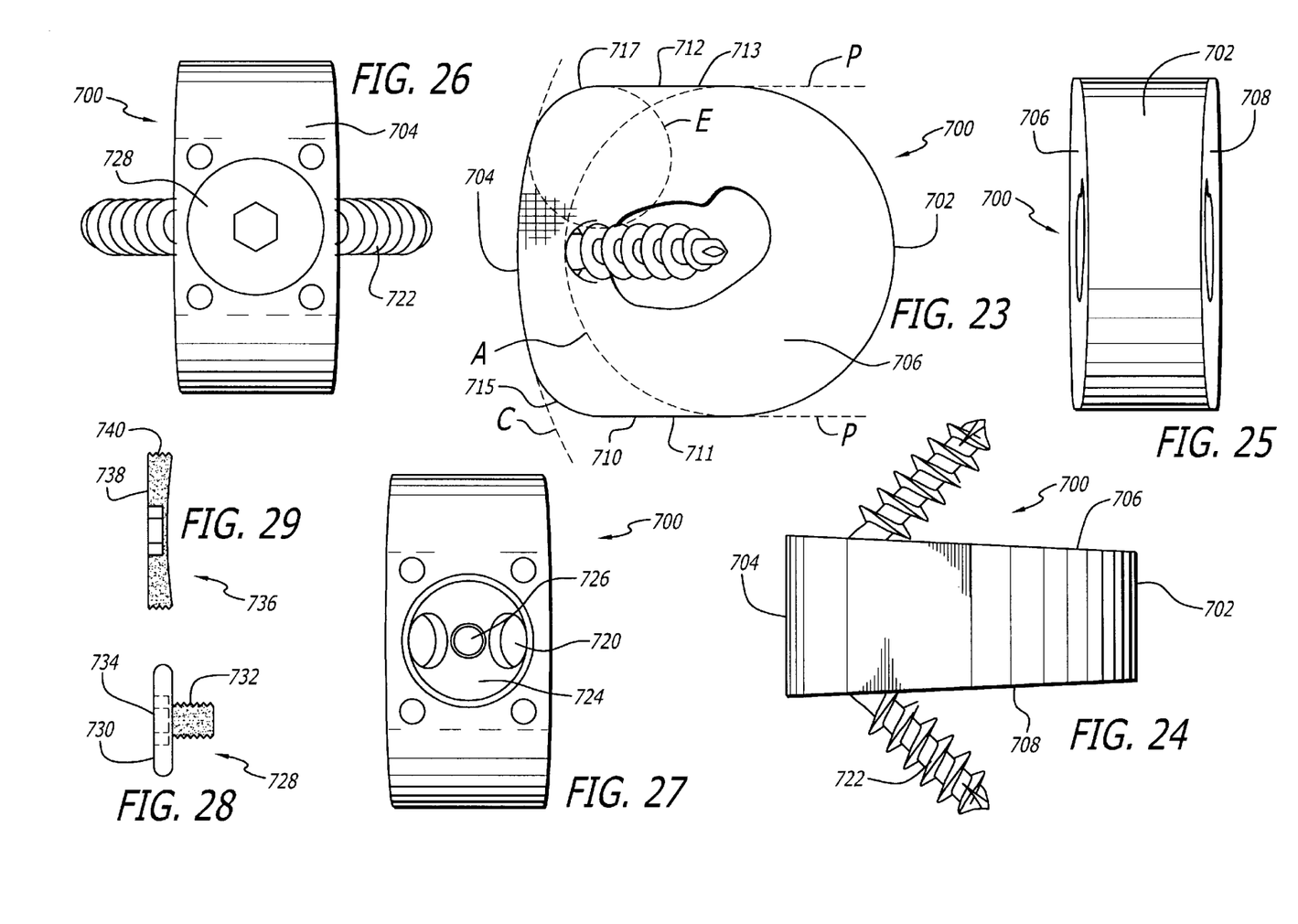
FIG. 23 is a top plan view of another preferred embodiment of a bone implant in accordance with the present invention with bone engaging screws.
FIG. 24 is a side elevation view of the implant of FIG. 23.
FIG. 25 is a leading end view of the implant of FIG. 23.
FIG. 26 is a trailing end view of the implant of FIG. 23 with the bone engaging screws and lock installed.
FIG. 27 is a trailing end view of the implant of FIG. 26 without the bone engaging screws and lock installed.
FIG. 28 is a partial cross sectional side view of a preferred embodiment of a bone screw lock in accordance with the present invention for use with the implant of FIG. 23.
FIG. 29 is a cross sectional side view of another preferred embodiment of a bone screw lock in accordance with the present invention.

Rounded portion 715, 717 may be an arc of a third circle E that preferably has a radius less than the radii of circle A associated with leading end 702 and/or circle C associated with trailing end 704.

In a preferred embodiment, implant 700 may be machined so as to be adapted to receive through bone screw receiving holes 720 at trailing end 704 at least a pair of opposed appropriately sized bone screws 722 preferably, but not necessarily, made of cortical bone. Bone engaging screws 722 may be aligned or offset from each other. At least one screw 722 engages each of the vertebral bodies adjacent a disc space to be fused and into which implant 700 is implanted. A purpose of the bone screws is to rigidly secure the implant within the vertebral segment. A further purpose is to pull each of the adjacent vertebral bodies toward the implant and towards each other. Trailing end 704 of implant 700 preferably includes a recess 724 having bone screw receiving holes 720 therein and an opening 726 configured to cooperatively receive a locking cap 728 adapted to lock at least one bone screw 722 to implant 700.

As shown in FIG. 28, implant 700 is preferably further machined and adapted to receive a lock 728, preferably made of cortical bone, at trailing end 704 for securing bone engaging screws 722 therein and preventing the screws from backing out. Locking cap 728 has a top 730, a stem 732, and a tool engagement area 734. In use, locking cap cooperatively engages trailing end 704 of implant 700 at opening 726 to lock at least one bone screw to implant 700. If desired, locking cap 728 may include a thread on stem 732 to allow locking cap 728 to rotationally engage implant 700.

FIG. 29 shows another preferred embodiment of a locking cap, generally referred to by the numeral 736. Locking cap 736 includes a top 738 having a thread 740 at its outer perimeter that is adapted to cooperatively engage a corresponding threaded recess in the implant.

The bone implant, bone screws, and/or locks can be made of a bioresorbable material, including but not limited to cortical bone, plastics and composite plastics. Suitable plastics may include those comprising lactides, galactides, glycolide, capronlactone, trimethylene carbonate, or dioxanone in various polymers, and/or combinations thereof.

By way of example only and not limitation, for use in the lumbar spine, the implants of the present invention may have a depth of approximately, 28–36 mm, a width of approximately, 30–38 mm, and a height (max) of approximately 8–20 mm. The radius of curvature of the leading end may be approximately 15–19 mm and the radius of curvature of the trailing end may be approximately 20–30 mm.

In any of the embodiments of the present invention, the implant may include, be made of, treated, coated, filled, used in combination with, or have a hollow or medullary canal for containing artificial or naturally occurring materials and/or substances suitable for implantation in the human spine. These materials and/or substances include any source of osteogenesis, bone growth promoting materials, bone, bone derived substances or products, demineralized bone matrix, mineralizing proteins, ossifying proteins, bone morphogenetic proteins, hydroxyapatite, genes coding for the production of bone, and bone including, but not limited to, cortical bone. The implant can include at least in part of materials that are bioabsorbable and/or resorbable in the body such as bone and/or bone growth promoting materials. The implant of the present invention can be formed of a porous material or can be formed of a material that intrinsically participates in the growth of bone from one of adjacent vertebral bodies to the other of adjacent vertebral bodies. Where such implants are for posterior implantation, the trailing ends of such implants may be treated with, coated with, or used in combination with chemical substances to inhibit scar tissue formation in the spinal canal. The implant of the present invention may be modified, or used in combination with materials to make it antibacterial, such as, but not limited to, electroplating or plasma spraying with silver ions or other substance. At least a portion of the implant may be treated to promote bone ingrowth between the implant and the adjacent vertebral bodies. The implant of the present invention may be used in combination with a spinal fixation implant such as any object, regardless of material, that can be inserted into any portion of the spine, such as but not limited to interbody spinal implants, structural bone grafts, mesh, cages, spacers, staples, bone screws, plates, rods, tethers of synthetic cords or wires, or other spinal fixation hardware While the shapes of the various aspects of the implant have been described precisely, the scope of the present invention is not so limited and it is readily anticipated that the contours may be interrupted by minor irregularities such as for example only for the purpose of engaging the bone, encouraging the ingrowth or through growth of bone.

While specific innovative features were presented in reference to specific examples, they are just examples, and it should be understood that various combinations of these innovative features beyond those specifically shown are taught such that they may now be easily alternatively combined and are hereby anticipated and claimed.

What is claimed is:

1. An interbody spinal implant made of cortical bone for insertion at least in part into an implantation space formed across the height of a disc space between adjacent vertebral bodies of a human spine, the vertebral bodies having an anterior aspect and a posterior aspect and a depth therebetween, said implant comprising:

a leading end for insertion first into the disc space and a trailing end opposite said leading end, said implant having a length from said leading end to said trailing end;

opposed upper and lower portions between said leading and trailing ends adapted to be placed at least in part within and across the height of the disc space to contact and support the adjacent vertebral bodies, said upper and lower portions being non-arcuate along at least a portion of the length of said implant; and opposite sides between said upper portion and said lower portion, and between said leading and trailing ends, said opposite sides defining a width of said implant, at least one of said opposite sides being at least in part straight along at least a portion of the length of said implant, said leading end configured in the shape of approximately one half of a circle from one of said opposite sides to another of said opposite sides, the circle having a diameter generally equal to the width of said implant;

said implant being manufactured from a bone ring obtained from a major long bone of a human having a medullary canal, said implant including at least a portion of the medullary canal passing through said upper and lower portions to form at least a portion of a passage adapted to hold bone growth promoting material for permitting for the growth of bone from vertebral body to vertebral body through said passage.

2. The implant of claim 1, wherein said implant has a maximum width between said opposite sides that is greater than one-half of the width of the adjacent vertebral bodies into which said implant is adapted to be inserted.

3. The implant of claim 1, wherein said implant has a maximum width between said opposite sides that is less than one-half of the width of the adjacent vertebral bodies into which said implant is adapted to be inserted.

4. The implant of claim 3, wherein said implant is adapted to be inserted side by side a second of said implant into the disc space between the adjacent vertebral bodies.

5. The implant of claim 1, wherein at least a portion of said leading end has a reduced height to facilitate insertion of said implant between the two adjacent vertebral bodies.

6. The implant of claim 1, wherein said trailing end is adapted to conform from side to side to at least a portion of the peripheral contour of at least one of the anterior and posterior aspects of the vertebral bodies adjacent a disc space into which said implant is inserted.

7. The implant of claim 1, wherein said passage is between said opposite sides of said implant.

8. The implant of claim 1, wherein said passage intersects at least one of said opposite sides.

9. The implant of claim 1, wherein said passage is between said leading and trailing ends of said implant.

10. The implant of claim 1, wherein said implant has a mid-longitudinal axis along the length, at least one of said opposite sides being at least in part oriented generally parallel to the mid-longitudinal axis of said implant.

11. The implant of claim 1, wherein said opposite sides are at least in part generally parallel one another.

12. The implant of claim 1, wherein at least a portion of said upper and lower surfaces are in an angular relationship to each other from trailing end to leading end for allowing angulation of the adjacent vertebral bodies relative to each other.

13. The implant of claim 1, wherein said implant has a maximum length less than and approximating the posterior to anterior depth of the vertebral bodies.

14. The implant of claim 1, further comprising a bone engaging surface formed on the exterior of at least said upper and lower portions for engaging the adjacent vertebral bodies, said bone engaging surface including at least one of a protrusion, a ratchet, a spike, a spline, surface roughenings, and knurling.

15. The implant of claim 1, wherein said implant includes at least two members, each member having a leading portion, a trailing portion, a top, a bottom, and at least one side, each member being adapted to be placed side by side with another of said members, said leading portion of said members forming said leading end of said implant when placed side by side.

16. The implant of claim 15, wherein said implant includes two of said members, each member being a mirror image of the other.

17. The implant of claim 15, wherein each member includes at least a portion of said passage.

18. The implant of claim 1, wherein said implant comprises at least in part of a bone growth promoting material.

19. The implant of claim 18, wherein said bone growth promoting material is selected from one of bone, bone derived products, demineralized bone matrix, mineralizing proteins, ossifying proteins, bone morphogenetic protein, hydroxyapatite, and genes coding for the production of bone.

20. The implant of claim 1, in combination with a bone growth promoting material.

21. The implant of claim 20, wherein said bone growth promoting material is selected from one of bone, bone derived products, demineralized bone matrix, mineralizing proteins, ossifying proteins, bone morphogenetic protein, hydroxyapatite, and genes coding for the production of bone.

22. The implant of claim 1, wherein said implant is treated with a bone growth promoting substance.

23. The implant of claim 1, wherein said implant is at least in part resorbable.

24. The implant of claim 1, in combination with a chemical substance adapted to inhibit scar formation.

25. The implant of claim 1, in combination with an antimicrobial material.

26. The implant of claim 1, wherein at least a portion of said implant is treated to promote bone ingrowth between said implant and said adjacent vertebral bodies.

27. The implant of claim 1, further in combination with at least one spinal fixation implant.

28. The implant of claim 1, wherein said trailing end is adapted to receive at least one bone screw adapted to engage at least one vertebral body when inserted through said implant.

29. The implant of claim 28, further comprising a lock for locking at least one bone screw to said implant.

30. The implant of claim 29, wherein said lock is made of one of cortical bone and a bioresorbable material.

31. The implant of claim 28, wherein said screw is made of one of cortical bone and a bioresorbable material.

32. An interbody spinal implant made of cortical bone for insertion at least in part into an implantation space formed across the height of a disc space between adjacent vertebral bodies of a human spine, the vertebral bodies having an anterior aspect and a posterior aspect and a depth therebetween, said implant comprising:

a leading end for insertion first into the disc space and a trailing end opposite said leading end, said implant having a length from said leading end to said trailing end;

opposed upper and lower portions between said leading and trailing ends adapted to be placed at least in part within and across the height of the disc space to contact and support the adjacent vertebral bodies;

said implant having a maximum width that is greater than one-half of the width of the adjacent vertebral bodies into which said implant is adapted to be inserted, said leading end configured in the shape of approximately one half of a first circle along the width of said implant, said trailing end having a radius of curvature of a second circle along the width of said implant, the second circle having a radius greater than the radius of the first circle; and said implant being manufactured from a bone ring obtained from a major long bone of a human having a medullary canal, maid implant including at least a portion of the medullary canal passing through said upper and lower portions to form a passage adapted to hold bone growth promoting material for permitting for the growth of bone from vertebral body to vertebral body through said passage.

33. The implant of claim 32, wherein said leading end and said trailing end of said implant intersect at diametrically opposite points of the implant.

34. The implant of claim 32, wherein said width of said implant is approximately equal to the diameter of the first circle.

35. The implant of claim 32, wherein said implant has a height from said upper portion to said lower portion, the height of said implant being less than the maximum width of said implant.

36. The implant of claim 32, wherein at least a portion of said leading end has a reduced height to facilitate insertion of said implant between the two adjacent vertebral bodies.

37. The implant of claim 32, wherein said trailing end is adapted to conform from side to side to at least a portion of the peripheral contour of at least one of the anterior and posterior aspects of the vertebral bodies adjacent a disc space into which said implant is inserted.

38. The implant of claim 32, wherein said implant has a perimeter, said passage being within said perimeter of said implant.

39. The implant of claim 32, wherein said implant has a perimeter, said passage intersecting at least a portion of said perimeter.

40. The implant of claim 32, wherein said passage is between said leading and trailing ends of said implant.

41. The implant of claim 32, further comprising opposite sides between said leading end and said trailing end.

42. The implant of claim 41, wherein at least one of said opposite sides is at least in part straight along at least a portion of the length of said implant.

43. The implant of claim 41, wherein said implant has a mid-longitudinal axis along the length, at least one of said opposite sides being at least in part oriented generally parallel to the mid-longitudinal axis of said implant.

44. The implant of claim 41, wherein said opposite sides are at least in part generally parallel one another.

45. The implant of claim 32, wherein at least a portion of said upper and lower surfaces are in an angular relationship to each other from trailing end to leading end for allowing angulation of the adjacent vertebral bodies relative to each other.

46. The implant of claim 32, wherein said implant has a maximum length less than and approximating the posterior to anterior depth of the vertebral bodies.

47. The implant of claim 32, further comprising a bone engaging surface formed on the exterior of at least said upper and lower portions for engaging the adjacent vertebral bodies, said bone engaging surface including at least one of a protrusion, a ratchet, a spike, a spline, surface roughenings, and knurling.

48. The implant of claim 32, wherein said implant includes at least two members, each member having a leading portion, a trailing portion, a top, a bottom, and at least one side, each member being adapted to be placed side by side with another of said members, said leading portion of said members forming said leading end of said implant when placed side by side.

49. The implant of claim 48, wherein said implant includes two of said members, each member being a mirror image of the other.

50. The implant of claim 48, wherein each member includes at least a portion of said passage.

51. The implant of claim 32, wherein said implant comprises at least in part of a bone growth promoting material.

52. The implant of claim 51, wherein said bone growth promoting material is selected from one of bone, bone derived products, demineralized bone matrix, mineralizing proteins, ossifying proteins, bone morphogenetic protein, hydroxyapatite, and genes coding for the production of bone.

53. The implant of claim 32, in combination with a bone growth promoting material.

54. The implant of claim 53, wherein said bone growth promoting material is selected from one of bone, bone derived products, demineralized bone matrix, mineralizing proteins, ossifying proteins, bone morphogenetic protein, hydroxyapatite, and genes coding for the production of bone.

55. The implant of claim 32, wherein said implant is treated with a bone growth promoting substance.

56. The implant of claim 32, wherein said implant is at least in part resorbable.

57. The implant of claim 32, in combination with a chemical substance adapted to inhibit scar formation.

58. The implant of claim 32, in combination with an antimicrobial material.

59. The implant of claim 32, wherein at least a portion of said implant is treated to promote bone ingrowth between said implant and said adjacent vertebral bodies.

60. The implant of claim 32, further in combination with at least one spinal fixation implant.

61. The implant of claim 41, further comprising a curved transition between at least one of said opposite sides and said trailing end, said curved transition forming at least part of an arc of a circle.

62. The implant of claim 32, wherein said trailing end is adapted to receive at least one bone screw adapted to engage at least one vertebral body when inserted through said implant.

63. The implant of claim 62, further comprising a lock for locking at least one bone screw to said implant.

64. The implant of claim 63, wherein said lock is made of one of cortical bone and a bioresorbable material.

65. The implant of claim 62, wherein said screw is made of one of cortical bone and a bioresorbable material.

66. An interbody spinal implant made of a bone composite material for insertion at least in part into an implantation space formed across the height of a disc space between adjacent vertebral bodies of a human spine, the vertebral bodies having an anterior aspect and a posterior aspect and a depth therebetween, said implant comprising:

a leading end for insertion first into the disc space and a trailing end opposite said leading end, said implant having a length from said leading end to said trailing end;

opposed upper and lower portions between said leading and trailing ends adapted to be placed at least in part within and across the height of the disc space to contact and support the adjacent vertebral bodies, said upper and lower portions being non-arcuate along at least a portion of the length of said implant;

opposite sides between said upper portion and said lower portion, and between said leading and trailing ends, said opposite sides defining a width of said implant, at least one of said opposite sides being at least in part straight along at least a portion of the length of said implant, said leading end configured in the shape of approximately one half a circle from one of said opposite sides to another of said opposite sides, the circle having a diameter generally equal to the width of said implant; and said implant being manufactured from a bone composite material, said upper and lower portions of said implant including at least one opening in communication with one another to form at least a portion of a passage adapted to hold bone growth promoting malarial for permitting for the growth of bone from vertebral body to vertebral body through said passage.

67. The implant of claim 66, wherein said bone composite material includes at least one of cortical bone fibers, bone filaments, bone particles and bone dust.

68. The implant of claim 66, further comprising a binding material.

69. The implant of claim 59, wherein said binding material is at least one of bioactive and bioresorbable.

70. The implant of claim 66, wherein said implant has a maximum width between said opposite sides that is greater than one-half of the width of the adjacent vertebral bodies into which said implant is adapted to be inserted.

71. The implant of claim 66, wherein said implant has a maximum width between said opposite sides that is less than one-half of the width of the adjacent vertebral bodies into which said implant is adapted to be inserted.

72. The implant of claim 71, wherein said implant is adapted to be inserted side by side a second of said implant into the disc space between the adjacent vertebral bodies.

73. The implant of claim 66, wherein at least a portion of said leading end is has a reduced height to facilitate insertion of said implant between the two adjacent vertebral bodies.

74. The implant of claim 66, wherein said trailing end is adapted to conform from side to side to at least a portion of the peripheral contour of at least one of the anterior and posterior aspects of the vertebral bodies adjacent a disc space into which said implant is inserted.

75. The implant of claim 66, wherein said passage is between said opposite sides of said implant.

76. The implant of claim 66, wherein said passage intersects at least one of said opposite sides of said implant.

77. The implant of claim 66, wherein said passage is between said leading and trailing ends of said implant.

78. The implant of claim 66, wherein said implant has a mid-longitudinal axis, at least one of said opposite sides being at least in part oriented generally parallel to the mid-longitudinal axis of said implant.

79. The implant of claim 66, wherein said opposite sides are at least in part generally parallel one another.

80. The implant of claim 66, wherein at least a portion of said upper and lower surfaces are in an angular relationship to each other from trailing end to leading end for allowing angulation of the adjacent vertebral bodies relative to each other.

81. The implant of claim 66, wherein said implant has a maximum length less than and approximating the posterior to anterior depth of the vertebral bodies.

82. The implant of claim 66, further comprising a bone engaging surface formed on the exterior of at least said upper and lower portions for engaging the adjacent vertebral bodies, said bone engaging surface including at least one of a protrusion, a ratchet, a spike, a spline, surface roughenings, and knurling.

83. The implant of claim 66, wherein said implant includes at least two members, each member having a leading portion, a trailing portion, a top, a bottom, and at least one side, each member being adapted to be placed side by side with another of said members, said leading portion of said members forming said leading end of said implant when placed side by side.

84. The implant of claim 83, wherein said implant includes two of said members, each member being a mirror image of the other.

85. The implant of claim 83, wherein each member includes at least a portion of said passage.

86. The implant of claim 66, wherein said implant comprises at least in part of a bone growth promoting material.

87. The implant of claim 86, wherein said bone growth promoting material is selected from one of bone, bone derived products, demineralized bone matrix, mineralizing proteins, ossifying proteins, bone morphogenetic protein, hydroxyapatite, and genes coding for the production of bone.

88. The implant of claim 66, in combination with a bone growth promoting material.

89. The implant of claim 88, wherein said bone growth promoting material is selected from one of bone, bone derived products, demineralized bone matrix, mineralizing proteins, ossifying proteins, bone morphogenetic protein, hydroxyapatite, and genes coding for the production of bone.

90. The implant of claim 66, wherein said implant is treated with a bone growth promoting substance.

91. The implant of claim 66, wherein said implant is at least in part resorbable.

92. The implant of claim 66, in combination with a chemical substance adapted to inhibit scar formation.

93. The implant of claim 66, in combination with an antimicrobial material.

94. The implant of claim 66, wherein at least a portion of said implant is treated to promote bone ingrowth between said implant and said adjacent vertebral bodies.

95. The implant of claim 66, further in combination with at least one spinal fixationimplant.

96. The implant of claim 66, wherein said trailing end is adapted to receive at least one bone screw adapted to engage at least one vertebral body when inserted through said implant.

97. The implant of claim 96, further comprising a lock for locking at least one bone screw to said implant.

98. The implant of claim 97, wherein said lock is made of one of cortical bone and a bioresorbable material.

99. The implant of claim 96, wherein said screw is made of one of cortical bone and a bioresorbable material.

100. An interbody spinal implant made of a bone composite material for insertion at least in part into an implantation space formed across the height of a disc space between adjacent vertebral bodies of a human spine, the vertebral bodies having an anterior aspect and a posterior aspect and a depth therebetween, said implant comprising:
  a leading end for insertion first into the disc space and a trailing end opposite said leading end, said implant having a length from said leading end to said trailing end;
  opposed upper and lower portions between said leading and trailing ends adapted to be placed at least in part within and across the height of the disc space to contact and support the adjacent vertebral bodies;
  said implant having a maximum width that is greater than one-half of the width of the adjacent vertebral bodies into which said implant is adapted to be inserted, said leading end configured in the shape of approximately one half of a first circle along the width of said implant, said trailing end having a radius of curvature of a second circle along the width of said implant, the second circle having a radius greater than the radius of the first circle; and
  said implant being manufactured from a bone composite material, said upper and lower portions of said implant including at least one opening in communication with one another to form a passage adapted to hold bone growth promoting material for permitting for the growth of bone from vertebral body to vertebral body through said passage.

101. The implant of claim 100, wherein said bone composite material includes at least one of cortical bone fibers, bone filaments, bone particles and bone dust.

102. The implant of claim 100, further comprising a binding material.

103. The implant of claim 102, wherein said binding material is at least one of bioactive and bioresorbable.

104. The implant of claim 100, wherein said leading end and said trailing end of said implant intersect at diametrically opposite points of the implant.

105. The implant of claim 100, wherein said width of said implant is approximately equal to the diameter of the first circle.

106. The implant of claim 100, wherein said implant has a height from said upper portion to said lower portion the height of said implant is less than the maximum width of said implant.

107. The implant of claim 100, wherein at least a portion of said leading end has a reduced height to facilitate insertion of said implant between the two adjacent vertebral bodies.

108. The implant of claim 100, wherein said trailing end is adapted to conform from side to side to at least a portion of the peripheral contour of at least one of the anterior and posterior aspects of the vertebral bodies adjacent a disc space into which said implant is inserted.

109. The implant of claim 100, wherein implant has a perimeter and said passage is at least in part within said perimeter of said implant.

110. The implant of claim 100, wherein said implant has a perimeter, said passage intersecting at least a portion of said perimeter of said implant.

111. The implant of claim 100, wherein said passage is between said leading and trailing ends of said implant.

112. The implant of claim 100, further comprising opposite sides between said leading end and said trailing end.

113. The implant of claim 112, wherein at least one of said opposite sides is at least in part straight along at least a portion of the length of said implant.

114. The implant of claim 112, wherein said implant has a mid-longitudinal axis along the length, at least one of said opposite sides being at least in part oriented generally parallel to the mid-longitudinal axis of said implant.

115. The implant of claim 112, wherein said opposite sides are at least in part generally parallel one another.

116. The implant of claim 100, wherein at least a portion of said upper and lower surfaces are in an angular relationship to each other from trailing end to leading end for allowing angulation of the adjacent vertebral bodies relative to each other.

117. The implant of claim 100, wherein said implant has a maximum length less than and approximating the posterior to anterior depth of the vertebral bodies.

118. The implant of claim 100, further comprising a bone engaging surface formed on the exterior of at least said upper and lower portions for engaging the adjacent vertebral bodies, said bone engaging surface including at least one of a protrusion, a ratchet, a spike, a spline, surface roughenings, and knurling.

119. The implant of claim 100, wherein said implant includes at least two members, each member having a leading portion, a trailing portion, a top, a bottom, and at least one side, each member being adapted to be placed side by side with another of said members, said leading portion of said members forming said leading end of said implant when placed side by side.

120. The implant of claim 119, wherein said implant includes two of said members, each member being a mirror image of the other.

121. The implant of claim 119, wherein each member includes at least a portion of said passage.

122. The implant of claim 100, wherein said implant comprises at least in part of a bone growth promoting material.

123. The implant of claim 122, wherein said bone growth promoting material is selected from one of bone, bone derived products, demineralized bone matrix, mineralizing proteins, ossifying proteins, bone morphogenetic protein, hydroxyapatite, and genes coding for the production of bone.

124. The implant of claim 100, in combination with a bone growth promoting material.

125. The implant of claim 124, wherein said bone growth promoting material is selected from one of bone, bone derived products, demineralized bone matrix, mineralizing proteins, ossifying proteins, bone morphogenetic protein, hydroxyapatite, and genes coding for the production of bone.

126. The implant of claim 100, wherein said implant is treated with a bone growth promoting substance.

127. The implant of claim 100, wherein said implant is at least in part resorbable.

128. The implant of claim 100, in combination with a chemical substance adapted to inhibit scar formation.

129. The implant of claim 100, in combination with an antimicrobial material.

130. The implant of claim 100, wherein at least a portion of said implant is treated to promote bone ingrowth between said implant and said adjacent vertebral bodies.

131. The implant of claim 100, further in combination with at least one spinal fixation implant.

132. The implant of claim 112, further comprising a curved transition between at least one of said opposite sides and said trailing end, said curved transition forming at least part of an arc of a circle.

133. The implant of claim 100, wherein said trailing end is adapted to receive at least one bone screw adapted to engage at least one vertebral body when inserted through said implant.

134. The implant of claim 133, further comprising a lock for locking at least one bone screw to said implant.

135. The implant of claim 134, wherein said lock is made of one of cortical bone and a bioresorbable material.

136. The implant of claim 133, wherein said screw is made of one of cortical bone and a bioresorbable material.

* * * * *

UNITED STATES PATENT AND TRADEMARK OFFICE
CERTIFICATE OF CORRECTION

PATENT NO. : 6,749,636 B2
DATED : June 15, 2004
INVENTOR(S) : Gary K. Michelson It is certified that error appears in the above-identified patent and that said Letters Patent is hereby corrected as shown below:

Column 12,
Line 53, change "maid" to -- said --.

Signed and Sealed this

Fourteenth Day of September, 2004

JON W. DUDAS
*Director of the United States Patent and Trademark Office*

UNITED STATES PATENT AND TRADEMARK OFFICE
CERTIFICATE OF CORRECTION

PATENT NO. : 6,749,636 B2 Page 1 of 1
DATED : June 15, 2004
INVENTOR(S) : Gary K. Michelson

It is certified that error appears in the above-identified patent and that said Letters Patent is hereby corrected as shown below:

Column 12,
Line 53, change "maid" to -- said --.

Column 14,
Line 58, change "malarial" to -- material --.

Signed and Sealed this

Fourteenth Day of December, 2004

JON W. DUDAS
*Director of the United States Patent and Trademark Office*